United States Patent
Fuhr

(10) Patent No.: US 7,029,705 B2
(45) Date of Patent: Apr. 18, 2006

(54) NASAL HYGIENE METHOD AND COMPOSITION

(76) Inventor: Allan H. Fuhr, 6669 Grand Orchid Way, Delray Beach, FL (US) 33446

( * ) Notice: Subject to any disclaimer, the term of this patent is extended or adjusted under 35 U.S.C. 154(b) by 51 days.

(21) Appl. No.: 10/630,453

(22) Filed: Jul. 30, 2003

(65) Prior Publication Data

US 2004/0071788 A1    Apr. 15, 2004

Related U.S. Application Data

(60) Provisional application No. 60/399,502, filed on Jul. 30, 2002.

(51) Int. Cl.
*A61K 7/00*    (2006.01)
*A61K 7/48*    (2006.01)
*A61K 33/06*   (2006.01)
*A61K 33/20*   (2006.01)
*A61K 33/14*   (2006.01)

(52) U.S. Cl. ............. 424/662; 424/661; 424/663; 424/664; 424/665; 424/677; 424/679; 424/680; 424/682; 424/684; 424/685; 424/686; 424/688; 424/689; 424/690; 424/691; 424/698; 424/717; 514/853; 510/109; 510/131; 510/383

(58) Field of Classification Search ........ 424/661–665, 424/679–680, 682, 684–686, 688–691, 698, 424/717, 677; 514/853; 510/109, 131, 383
See application file for complete search history.

(56) References Cited

U.S. PATENT DOCUMENTS

| | | | | |
|---|---|---|---|---|
| 5,334,383 A | * | 8/1994 | Morrow | 424/94.4 |
| 5,622,848 A | * | 4/1997 | Morrow | 435/173.1 |
| 5,736,165 A | * | 4/1998 | Ripley et al. | 424/661 |
| 6,387,344 B1 | * | 5/2002 | Tenney et al. | 423/478 |

OTHER PUBLICATIONS

Chemical Abstracts 136:74583; abstracting CN 1296819 (2001).*

* cited by examiner

*Primary Examiner*—John Pak
(74) *Attorney, Agent, or Firm*—Robert M. Schwartz

(57) ABSTRACT

A method is disclosed of practicing nasal hygiene comprising the steps of applying to a person's nostril a non-irritating hygienic composition consisting essentially of a product of compounding under homogenizing conditions water, 0.01% to 5% by weight, as chlorine dioxide, of a source of chlorine dioxide; 0.01% to 3% by weight of at least one olfactory stimulant, 0 to 5% by weight of at least one fixative compound less volatile than the olfactory stimulant 0.1 to 2.5% by weight of at least one inorganic salt selected from the group consisting of alkali metal chloride, alkali metal bicarbonate, and alkali metal chlorate; and 0.0002 to 0.006% (as aluminum) by weight of at least one water soluble aluminum compound, provided that the total concentration of inorganic salt is in the range from 0.6% by weight to 2.5% by weight, holding the composition within the nostril for a hygienic holding period, and discharging the composition from the treated nostril.

21 Claims, No Drawings

NASAL HYGIENE METHOD AND COMPOSITION

CROSS REFERENCE TO RELATED APPLICATIONS

This application claims the benefit of U.S. Provisional Application No. 60/399,502, filed on Jul. 30, 2002, entitled NASAL HYGIENE METHOD AND COMPOSITION.

BACKGROUND OF THE INVENTION

This invention relates to a method of practicing hygiene of the human nose and a composition for use in practice of the method of the invention.

In the United States and other so-called Western nations, nasal hygiene is rarely practiced as a daily or even frequent periodic routine. "Keeping one's nose clean" is usually understood metaphorically to mean the endeavor to avoid giving offense to others. In some parts of the world, nasal hygiene is as routine as brushing one's teeth.

There is still uncertainty of what might be used to accomplish effective nasal hygiene in a convenient and non-irritating way.

Plain water, the universal cleanser, turns out to be a poor choice. As pointed out by Douglas Hoffman MD, while salt solutions containing higher concentrations than body tissues (so-called hypertonic solutions) draw water out of the tissues, plain water has the opposite effect, entering the tissues and adding to the swelling pressure. Saline solutions, on the other hand, need careful regulation to avoid levels of salt that irritate healthy and particularly inflamed tissues.

In ear-nose-throat clinics, patients have had noses rinsed with dilute potassium permanganate solutions for disinfecting purposes. This procedure required using large volumes of rinse solution, and users underwent the inconvenience of catching and disposing of the spent solution after use.

SUMMARY OF THE INVENTION

In accordance with this invention, there is provided a method of practicing nasal hygiene comprising the steps of applying to a person's nostril a non-irritating hygienic composition consisting essentially of a product of compounding under homogenizing conditions water, 0.01% to 5% by weight, as chlorine dioxide, of a source of chlorine dioxide; 0.01% to 3% by weight of at least one olfactory stimulant, 0 to 5% by weight of at least one fixative compound less volatile than the olfactory stimulant 0.1 to 2.5% by weight of at least one inorganic salt selected from the group consisting of alkali metal chloride, alkali metal bicarbonate, and alkali metal chlorate; and 0.0002 to 0.006% (as aluminum) by weight of at least one water soluble aluminum compound, provided that the total concentration of inorganic salt is in the range from 0.6% by weight to 2.5% by weight, holding the composition within the nostril for a hygienic holding period, and discharging the composition from the treated nostril.

There is also provided, in accordance with this invention, a novel non-irritating hygienic composition consisting essentially of a product of compounding under homogenizing conditions water, 0.01% to 5% by weight, as chlorine dioxide, of a source of chlorine dioxide; 0.01% to 3% by weight of at least one olfactory stimulant, 0 to 5% by weight of at least one fixative compound less volatile than the olfactory stimulant. 0.1 to 2.5% by weight of at least one inorganic salt selected from the group consisting of alkali metal chloride, alkali metal bicarbonate, and alkali metal chlorate; and 0.0002 to 0.006% (as aluminum) by weight of at least one water soluble aluminum compound, provided that the total concentration of inorganic salt is in the range from 0.6% by weight to 2.5% by weight.

It has been found that the ingredients of the composition interact cooperatively to provide an enhanced beneficial effect to the user beyond the individual effect of each individual ingredient. The nature of the interaction is not fully understood. It can be seen by chemical analysis that the measurable content of chlorine dioxide diminishes with time, while the effectiveness of the composition remains substantially undiminished even in compositions in which chlorine dioxide can no longer be detected. A hypothesis that chlorine dioxide is not essential to the activity of the composition is disproved by comparison of the effectiveness of a composition of the invention to an otherwise identical composition from which chlorine dioxide has been omitted. It is believed that chlorine dioxide functions in the composition of the invention by activating and enhancing the effectiveness of one or more other components of the composition, and may be diminished in concentration while doing so.

The term "consisting essentially of" is used in its art-recognized meaning to indicate that the composition is open only to such additional ingredients as do not adversely affect its beneficial properties. In particular, such ingredients, and concentrations of ingredients, as render the composition irritating to the mucous membrane inside the nose, are excluded. As an example of an additional ingredient that does not adversely affect the beneficial properties and can enhance the benefit of the composition, a fixative compound less volatile than the olfactory stimulant is given.

The term "product compounded under homogenizing conditions" defines a product that has been subjected to heat treatment and mechanical action sufficient to minimize a tendency to separate into two liquid phases. Heat treatment at moderately elevated temperatures in the range of 30 to 55° C. for a period of 1 to 2000 seconds is generally sufficient. Equipment for applying mechanical action is well known in the art and commercially available.

By practicing nasal hygiene by the use of the method and composition of the invention, the likelihood of sinusitis is reduced. Daily flushing or washing out the nose according to the invention clears away foreign debris, controls nasal odors, decreases the feeling of stuffiness, promotes healing after nasal surgery, and removes pollutants and bacteria that lead to sinus infection and allergies. The effectiveness of the method of the invention in diminishing bacterial levels in the user's nose can be ascertained by familiar bacteriological techniques.

Persons affected by stuffy nose can be soothed, decongested, and overcome dryness by treatment of the nose according to the invention.

DESCRIPTION OF PREFERRED EMBODIMENTS

A source of chlorine dioxide can be chlorine dioxide gas; a water soluble metal chlorite, especially an alkali metal chlorite; a combination of chlorine dioxide and such metal chlorite at a pH at which chlorine dioxide and chlorite ion coexist, i.e. at a pH in the range from 6 to 9; or a combination of such metal chlorite and a compound able to enhance the yield of chlorine dioxide obtainable from such metal chlorite. In an alkali metal chlorite, the alkali metal can be lithium, sodium, potassium, and mixtures thereof. Within the stated pH range, an inverse relationship exists between the reactivity of the combination of such metal chlorite and chlorine dioxide and the length of time it is stable; the higher the pH the more stable and less reactive.

As is known in the art, the generation of chlorine dioxide from alkali metal chlorite involves a valence change or oxidation of the formally 3-valent chlorine of chlorite ion to formally 4-valent chlorine of chlorine dioxide. In the absence of other oxidants, a chlorite ion can oxidize another chlorite ion to form chlorine dioxide, according to a reaction in which five chlorite ions yield four molecules of chlorine dioxide and a chloride ion. In the presence of added oxidants such as chlorine gas or hypochlorite ion, each chlorite ion is oxidized to a molecule of chlorine dioxide, so that chlorine and hypochlorite function to enhance the yield of chlorine dioxide obtainable from a metal chlorite. Generation of chlorine dioxide from a metal chlorite is also assisted by adjustment of the pH to lower (i.e. more acidic) values. Any acid can be used to make such pH adjustment, but mild acids such as acetic acid and citric acid are preferred.

The art has found certain techniques and additives helpful in increasing the stability of chlorine dioxide containing solution at a given pH within this range. Thus McNicolas U.S. Pat. No. 3,271,242 disclosed heat treatment of a solution of chlorine dioxide and sodium perborate or sodium carbonate peroxide at pH 6.8 to 7.2, the desired range for antiseptic purposes, at 75–92° for approximately 45 minutes with agitation, until a test for free peroxide is negative. Certain solutions containing chlorine dioxide and/or alkali metal chlorite together with various stabilizing additives including but not limited to salts of transition metals and post-transition metals are commercially available under such designations as Stabilized Chlorine Dioxide and even Stabilized Oxygen. The strength of such a solution is usually stated in terms of chlorine dioxide even if the active ingredient is nearly all alkali chlorite. A procedure for the preparation of a chlorine dioxide source solution from sodium chlorite and sodium hypochlorite is disclosed by J L Richter in U.S. Pat. No. 5,738,840. A generating apparatus for mixing predetermined quantities of water, sodium chlorite, and sodium hypochlorite to provide safe working concentrations of chlorine dioxide is offered by the Vernagene Division of Verna Limited, Bolton, England.

Accordingly, the composition of the invention includes sufficient chlorine dioxide source as defined to provide 0.01 to 5% by weight chlorine dioxide upon conversion thereto, preferably 0.1 to 2% by weight.

The olfactory stimulant ingredient can be a cycloaliphatic alcohol, a cycloaliphatic ketone, an aromaticnon-phenolic hydroxyl compound, an aromatic ether, a phenol having nine or more carbon atoms, or a mixture of such compounds. The olfactory stimulant ingredient can also be a mixture of volatile oils or ethereal oils derived from plant materials.

Illustrative cycloaliphatic alcohols include cyclododecanol, 3,3,5-trimethylcyclohexanol, and 4-t-butylcyclohexanol. Illustrative cycloaliphatic ketones include exaltone, fenchone, isophorone, muscone, and 3,3,5-trimethylcyclohexanone. Illustrative aromatic non-phenolic hydroxyl compounds include 1-phenylethanol, 2-phenylethanol, and 1-phenoxy-2-propanol. Illustrative aromatic ethers include diphenyl ether and 2-methoxynaphthalene. Illustrative phenols include p-t-octylphenol and 2,6-di-t-butyl-4-methylphenol.

Particularly preferred olfactory stimulant ingredients include thymol, eucalyptol, borneol, menthol, camphor, oil of eucalyptus, pine oil, and gum benzoin. Fixative compound when present is less volatile than the olfactory stimulant ingredient and can be, for example, an essential oil. Particularly preferred fixative compounds include oil of sweet birch, oil of spearmint, oil of pine, and cinnamon.

Certain oils extracted from plant materials include olfactory stimulants compounds as well as less volatile fixative type compounds and can serve as sources of both. Particularly preferred dual function oils of this type include basil, bergamot, citrus, jasmine, lemongrass, rosemary, sage, thyme, and vanilla.

The quantity of olfactory stimulant material in the composition of the invention is in the range from 0.01% to 3% by weight, preferably in the range from 0.05% to 1% by weight. The quantity of fixative material when present is in the range from 0.01% to 5% by weight, preferably in the range from 0.05% to 1% by weight.

The inorganic salt ingredients of the composition, i.e. alkali metal chloride, alkali metal bicarbonate, and alkali metal chlorate, can be lithium salts, potassium salts, sodium salts, and mixtures thereof. When salts of different metals are used together, for example a sodium salt and a potassium salt, ionization in the solution can associate a metal ion with the anion of a different salt from that supplied with the metal. Thus, a solution in which potassium bicarbonate and sodium chloride are dissolved contains potassium chloride as well as potassium bicarbonate, and sodium bicarbonate as well as sodium chloride.

Without intending to be bound by any theory, it is believed that the inorganic salt ingredient of the composition provides a multiplicity of functions, including adjusting the osmotic strength and the pH of the composition, and limiting the amount of water passing into the mucous membrane while enhancing the cleansing effect. It is therefore preferred to use a combination of two or more inorganic salts according to the invention.

The quantity of each inorganic salt in the composition of the invention is in the range from 0.1% to 2.5% by weight, preferably from 0.3% to 2% by weight, provided that the combined quantity of inorganic salts in the composition of the invention is in the range from 0.6% to 2.5% by weight.

The water soluble aluminum compound can be, for example, aluminum lactate, aluminum nitrate, aluminum sulfate, ammonium aluminum sulfate (ammonium alum) sodium aluminum sulfate (sodium alum), potassium aluminum sulfate (potassium alum) and mixtures thereof. Potassium alum is preferred. Ionization in the solution can associate aluminum with other anions such as chloride when present.

The quantity of water soluble aluminum salt in the composition of the invention, calculated as aluminum, is in the range from 0.0002% by weight to 0.01% by weight (corresponding to 2–100 parts per million), preferably in the range from 0.0005% by weight to 0.005% by weight (5 to 50 parts per million).

Without intending to be bound by any theory, it is believed that the modest levels of water soluble aluminum compound present act to enhance the effectiveness of the other ingredients with the result that considerably diminished quantities of the other ingredients, particularly olfactory stimulants and inorganic salts, are required for maximum effectiveness in nasal prophylaxis.

Optional adjuvants that can be included in low concentrations, typically less than 0.5%, in the composition of the invention to impart desired characteristics include colorants illustrated by sodium copper chlorophyllin, surface active materials illustrated by Polysorbate 80 (an ethoxylated sorbitan ester), and chelating agents illustrated by sodium citrate.

It is a feature of the invention that the practice of nasal hygiene according to the invention requires only moderate and convenient quantities of the composition. It is sufficient for the user to place a convenient quantity of the composition, which can range from about 0.3 to 3 milliliters, into each nostril and retain it for a holding period which can range from a fraction of a minute to about ten minutes or as long as comfortable, and then remove it as by blowing the nose. Any suitable applicator can be used to place the composition inside the user's nose.

EXAMPLE 1

A nasal hygiene composition according to the invention was prepared by mixing a commercial water solution of Stabilized Chlorine Dioxide containing approximately 2% by weight of $ClO_2$ with a solution containing the following ingredients in proportions to provide one part by volume of the Stabilized Chlorine Dioxide solution to nine parts by volume of solutions having concentrations (in % by weight) as shown:

| | |
|---|---|
| Thymol | 0.98 |
| Eucalyptol | 0.18 |
| Menthol | 0.21 |
| Camphor | 0.012 |
| Gum Benzoin | 0.03 |
| Potassium Alum | 0.01 |
| Potassium Chlorate | 0.32 |
| Sodium Bicarbonate | 0.83 |
| Sodium Chloride | 0.46 |
| Oil of Sweet Birch | 0.93 |
| Oil Spearmint | 1.02 |
| Oil Pine | 0.45 |
| Oil Cinnamon | 0.24 |
| Water | balance to 100 |

With about three quarters of the quantity of water reserved, the above ingredients were warmed to 40° C. and passed through an APV Homogenator (APV Crepaco Co, Rosemont Ill. 60018) operating at 29000 psi. This mechanical treatment yielded a light yellow liquid. Addition of the reserved quantity of water yielded a colorless homogeneous solution.

EXAMPLE 2

Portions of the solution prepared as in Example 1 were packaged in two ounce plastic bottles fitted with a pump nozzle and dip tube capable of delivering approximately two milliliters into a nostril with one squeeze of the bottle. This quantity of solution is more than sufficient to fill the entire nasal passage and the excess can be allowed to run back into the throat or drop out of the nose to be spilled. The composition can safely be swallowed although there is no intention and no need for the user to do so.

What is claimed is:

1. A non-irritating hygienic composition consisting essentially of the product of compounding under homogenizing conditions
water;
an amount of a source of chlorine dioxide sufficient to generate or provide 0.01% to 5% by weight of chlorine dioxide, 0.01 to 3% by weight of at least one olfactory stimulant, 0 to 5% by weight of at least one fixative compound less volatile than the olfactory stimulant, 0.1 to 2.5% by weight of at least one inorganic salt selected from the group consisting of alkali metal chloride, alkali metal bicarbonate, and alkali metal chlorate; and 0.0002 to 0.006% (as aluminum) by weight of at least one water soluble aluminum compound, provided that the total concentration of said at least one inorganic salt is in the range from 0.6% by weight to 2.5% by weight.

2. The hygienic composition of claim 1 having a pH in the range from 6 to 9.

3. The hygienic composition of claim 1, wherein the concentration of chlorine dioxide source is sufficient to generate or provide 0.1% to 2% by weight of chlorine dioxide.

4. The hygienic composition of claim 1, wherein the concentration of olfactory stimulant is in the range of 0.05 to 1% by weight.

5. The hygienic composition of claim 1, wherein at least two inorganic salts are present.

6. The hygienic composition of claim 1, wherein the concentration of water soluble aluminum compound is in the range of 0.0005% to 0.005% by weight.

7. The hygienic composition of claim 1, wherein the source of chlorine dioxide is an alkali metal chlorite.

8. The hygienic composition of claim 1, wherein the source of chlorine dioxide is a combination of alkali metal chlorite and chlorine dioxide.

9. The hygienic composition of claim 1, wherein the olfactory stimulant is selected from the group consisting of cycloaliphatic alcohols, cycloaliphatic ketones, non-phenolic aromatic hydroxyl compounds, phenols having at least nine carbon atoms, volatile oils derived from plant materials, and mixtures thereof.

10. The hygienic composition of claim 1, including 0.05% to 1% by weight of a fixative compound selected from the group consisting of oil of sweet birch, oil of spearmint, oil of pine, and mixtures thereof.

11. The hygienic composition of claim 1, wherein the water soluble aluminum compound is potassium aluminum sulfate.

12. The hygienic composition of claim 1, wherein said at least one inorganic salt is sodium bicarbonate.

13. The hygienic composition of claim 1, wherein said at least one inorganic salt is potassium chlorate.

14. The hygienic composition of claim 1, additionally containing an amount not exceeding 0.5% by weight of an adjuvant selected from the group consisting of colorants, surfactants, and chelating agents.

15. The hygienic composition of claim 1, wherein chlorine dioxide can be detected.

16. The hygienic composition of claim 1, wherein chlorine dioxide cannot be detected.

17. The composition of claim 1, wherein said source of chlorine dioxide is chlorine dioxide.

18. A method of practicing nasal hygiene comprising the steps of applying to a person's nostril a non-irritating hygienic composition consisting essentially of the product of compounding under homogenizing conditions water, an amount of a source of chlorine dioxide sufficient to generate or provide 0.01% to 5% by weight of chlorine dioxide, 0.01 to 3% by weight of at least one olfactory stimulant; 0 to 5% by weight of at least one fixative compound less volatile than the olfactory stimulant; 0.1 to 2.5% by weight of at least one inorganic salt selected from the group consisting of alkali metal chloride, alkali metal bicarbonate, and alkali metal chlorate; and 0.0002 to 0.006% (as aluminum) by weight of at least one water soluble aluminum compound, provided that the total concentration of said at least one inorganic salt is in the range from 0.6% by weight to 2.5% by weight, holding the composition within the nostril for a hygienic holding period, and discharging the composition from the treated nostril.

19. The method of claim 18, wherein the quantity of the hygienic composition applied to a nostril is in the range of 0.3 milliliters to 3 milliliters.

20. The method of claim 18, wherein the holding period is in the range from ten seconds to ten minutes.

21. The method of claim 18, wherein said source of chlorine dioxide is chlorine dioxide.

* * * * *